United States Patent
Moszner et al.

(10) Patent No.: US 7,078,446 B2
(45) Date of Patent: Jul. 18, 2006

(54) (METH) ACRYLATE-SUBSTITUTED IMINOOXIDIAZINE DIONE DERIVATIVES

(75) Inventors: Norbert Moszner, Eschen (LI); Thomas Völkel, Oberreitnau (DE); Urs Karl Fischer, Arbon (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 420 days.

(21) Appl. No.: 10/361,961

(22) Filed: Feb. 10, 2003

(65) Prior Publication Data

US 2003/0187091 A1    Oct. 2, 2003

(30) Foreign Application Priority Data

Feb. 27, 2002 (DE) ................ 102 08 395

(51) Int. Cl.
*A61K 6/083* (2006.01)
*A61C 5/00* (2006.01)
*C08G 18/04* (2006.01)

(52) U.S. Cl. .............. 523/116; 523/118; 528/73; 433/228.1

(58) Field of Classification Search .......... 523/116, 523/118; 528/73; 540/202; 433/228.1
See application file for complete search history.

(56) References Cited

U.S. PATENT DOCUMENTS

| | | | | |
|---|---|---|---|---|
| 5,914,383 | A * | 6/1999 | Richter et al. ............... 528/59 |
| 6,191,181 | B1 * | 2/2001 | Weikard et al. ............. 522/174 |
| 6,818,725 | B1 * | 11/2004 | Klare et al. .................. 528/73 |

FOREIGN PATENT DOCUMENTS

| | | |
|---|---|---|
| DE | 2 411 760 | 3/1974 |
| DE | 197 34 048 A1 | 8/1997 |
| EP | 0 209 365 A2 | 1/1987 |
| EP | 0 266 589 A1 | 10/1987 |
| EP | 0 273 245 A1 | 12/1987 |
| EP | 0 262 488 A1 | 4/1988 |
| EP | 0 798 299 A1 | 3/1997 |
| EP | 1 002 818 A1 | 5/2000 |

OTHER PUBLICATIONS

Richter et al., "Isocyanate and Isomeric," *Farbe & Lack* 106:60-72 (2000).

* cited by examiner

*Primary Examiner*—Tae H. Yoon
(74) *Attorney, Agent, or Firm*—Nixon Peabody LLP

(57) ABSTRACT

The invention relates to iminooxadiazine dione derivatives with the formula (I)

in which X, Y and Z represent a (meth)acrylic acid radical of the formula (II)

$$(CH_2=C(R^2)-COO)_n R^1-$$

in which $R^1$ is hydrogen, an aliphatic hydrocarbon radical with 1 to 14 carbon atoms, which can be interrupted by oxygen atoms, or an aromatic hydrocarbon radical with to 16 carbon atoms; $R^2$ is hydrogen, an aliphatic hydrocarbon radical with 1 to 5 carbon atoms or an aromatic hydrocarbon radical with 6 carbon atoms, n is 1 or 2; where the (meth) acrylic acid radical of formula (II) is bound to the radical of formula (I) by $R^1$ or $R^2$ and the binding point remaining at $R^2$ or $R^1$ is saturated by hydrogen and X, Y and Z can be the same or different; the individual radicals R being able to be the same or different and selected from alicyclic or aromatic hydrocarbon radicals with 5 to 10 or aliphatic hydrocarbon radicals with 1 to 10 carbon atoms.

12 Claims, No Drawings

(METH) ACRYLATE-SUBSTITUTED IMINOOXIDIAZINE DIONE DERIVATIVES

The present invention relates to iminooxadiazine dione derivatives which are substituted with (meth)acrylate radicals and which are effective as cross-linkers during radical polymerization.

Urethane (meth)acrylates are widely used as a constituent of adhesives, coatings and dental materials (cf. among others R. Holman (Ed.), UV and EB Curing Formulation for Printing Inks, Coatings and Paints, SITA-Technology, London 1984, 27; J. P. Fouassier, J. F. Rabek (Ed.), Radiation Curing in Polymer Science and Technology, Vol. IV, Elsevier Applied Science, London and New York 1993, 387). In the field of dentistry the monomer UDMA is mostly used which is accessible by reaction of 1 mol 2,2,4-trimethyl hexamethylene diisocyanate with 2 mol 2-hydroxyethyl methacrylate (HEMA). UDMA is often used in combination with bisphenol-A-diglycidyl methacrylate (bis-GMA), the addition product of methacrylic acid and bisphenol-A-diglycidyl ether (cf. among others DE-A-24 11 760). The reason for this is above all the good mechanical properties that can be achieved with bis-GMA.

EP 0 266 589 A1 and EP 0 273 245 A1 respectively disclose (meth)acrylic acid derivatives of cycloaliphatic and aliphatic triisocyanates which are accessible for example by reaction of 3 mol HEMA with 1 mol triisocyanate. The tri- or hexamethacrylate urethane derivatives obtained are said to result in dental composites with high resistance to abrasion.

Furthermore the reaction of 1 mol triisocyanate isocyanurate, e.g. of the trimer of hexamethylene diisocyanate (HDI), with 1 mol HEMA and 2 mol GDMA to produce a monomer with five polymerizable groups was reported (S. B. Mitra (ACS, Div. Polym. Chem., Poly. Prepr. 38 (2) (1997), 103). Cyanuric acid and isocyanuric acid derivatives are also called symmetric diisocyanate trimers.

Asymmetric isocyanate trimers and processes for their preparation are known from DE 197 34 048 A1 and EP 0 798 299 A1. The asymmetric trimers have a low viscosity and are therefore said to be particularly suitable for the preparation of varnishes with a reduced solvent content. In addition the compounds are said to show a low sensitivity vis-à-vis atmospheric moisture (see also F. Richter, H. Mertes, Farbe & Lacke 106 (2000) 60).

The object of the invention is to make available radically polymerizable monomers which result in polymerization products with good mechanical properties and are suitable in particular for the preparation of dental materials.

According to the invention this object is achieved by iminooxadiazine dione derivatives with the formula (I), in which

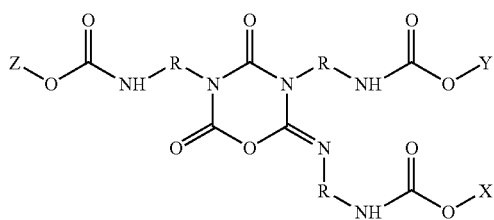

X, Y and Z represent a (meth)acrylic acid radical of the formula (II)

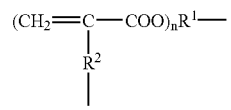

in which $R^1$ is hydrogen, an aliphatic hydrocarbon radical with 1 to 14 carbon atoms, preferably 2 to 5 carbon atoms, which can be interrupted by oxygen atoms, or an aromatic hydrocarbon radical with 6 to 16 carbon atoms, preferably 6 carbon atoms;

$R_2$ is hydrogen, an aliphatic hydrocarbon radical with 1 to 5 carbon atoms, preferably 1 carbon atom, or an aromatic hydrocarbon radical with 6 carbon atoms, only one of the radicals $R^1$ and $R^2$ being able to represent hydrogen;

n is 1 or 2;

where the (meth)acrylic acid ester of formula (II) is bound to the radical of formula (I) via $R^1$ or $R^2$ and the binding point remaining at $R^2$ or $R^1$ is saturated by hydrogen and where X, Y and Z can be the same or different;

the individual radicals R can be the same or different and are selected from alicyclic or aromatic hydrocarbon radicals with 5 to 10, preferably 7 to 10 carbon atoms, or from aliphatic hydrocarbon radicals with 1 to 10 carbon atoms, preferably 6 to 9 carbon atoms.

The radical of formula (II) is here also called (meth)acrylic radical for the sake of simplicity if $R^2$ is neither H nor $CH_3$, although strictly speaking in this case formula (II) represents acrylate radicals substituted in α-position.

According to the invention, by aliphatic hydrocarbon radicals are meant groups which derive from branched or unbranched alkanes by the removal of one to three hydrogen atoms.

Alicyclic hydrocarbon radicals are accordingly derived from the cycloalkanes, preferably from monocyclic cycloalkanes, cycloalkanes which are substituted with alkyl groups also being included according to the invention. In the case of alkyl-substituted cycloalkanes the hydrogen atom(s) can be removed from ring-positioned carbon atoms or from carbon atoms of the substituent(s), i.e. a coupling can take place via ring-positioned carbon atoms or via carbon atoms of the side chain. Preferred alicyclic hydrocarbon radicals are substituted or unsubstituted cyclohexane radicals. The preferred substituent is methyl.

By aromatic hydrocarbon radicals are meant benzene radicals and radicals which contain several condensed benzene rings. The benzene rings can be substituted with alkyl groups (alkylaryl radicals). In the case of alkyl-substituted aromatic radicals the hydrogen atoms can be removed from ring-positioned carbon atoms, such as e.g. in the case of the methylphenyl radical, or from carbon atoms of the substituent(s), such as e.g. in the case of the benzyl radical, i.e. a coupling can occur via ring-positioned carbon atoms or via carbon atoms of the side chain. Preferred aromatic hydrocarbon radicals are substituted or unsubstituted benzene radicals. The preferred substituent is methyl.

The (meth)acrylic acid radical of formula (II) preferably has a structure of the formula (IIa), (IIb) or (IIc),

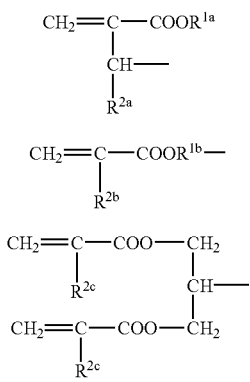

Formula IIa

Formula IIb

Formula IIc where the radicals present in the formulae (IIa); (IIb) and (IIc) independently of each other preferably have one of the following meanings:

$R^{1a}$: hydrogen or a straight-chained $C_1$ to $C_{12}$ alkyl radical, in particular $C_1$ to $C_4$ alkyl radical, a $C_6$ to $C_{12}$ aryl radical, in particular $C_6$ aryl radical, or $C_7$ to $C_{16}$ alkylaryl radical, in particular $C_7$ to $C_9$ alkylaryl radical;

$R^{2a}$: hydrogen, a $C_1$ to $C_5$ alkyl radical or a phenyl radical;

$R^{1b}$: is a $C_1$ to $C_{14}$ alkylene radical which can be interrupted by oxygen atoms, or a phenylene radical;

$R^{2b}$: hydrogen or a methyl radical;

$R^{2c}$: hydrogen or a methyl radical.

The variable n is 1 in the case of formulae (IIa) and (IIb), 2 in the case of formula (IIc).

The radicals R are preferably selected from the group which consists of the hexamethylene, 2,2,4-trimethylhexamethylene, 2,4,4-trimethylhexamethylene, m-toluylene, m-xylylene and isophorone radical:

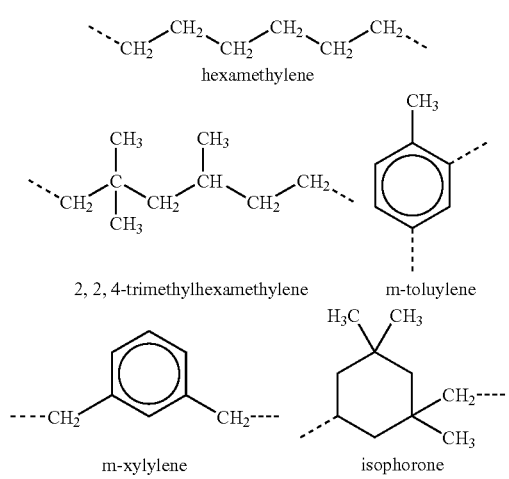

Iminooxadiazine dione derivatives according to formula (I) are particularly preferred in which the (meth)acrylic radical is a radical according to the formula IIa, IIb and/or IIc and at least one of the other radicals has the following meaning R=hexamethylene, 2,2,4-trimethylhexamethylene, 2,4,4 trimethylhexamethylene or m-toluylene;

$R^{1a}$=methyl, ethyl, benzyl or phenyl;

$R^{2a}$=hydrogen or methyl;

$R^{1b}$=ethylene, methylethylene or propylene;

$R^{2b}$=hydrogen or methyl;

$R^{2c}$=hydrogen or methyl.

Quite particularly preferred are naturally those iminooxadiazine dione derivatives in which all radicals have one of the named preferred and in particular one of the named particularly preferred meanings.

The iminooxadiazine dione derivatives according to the invention each have, depending on the choice of the groups X, Y and Z, 3 to 6 radically polymerizable (meth)acrylate groups, a control of the cross-linking density of the cured material being possible via the number of the polymerizable groups. X, Y and Z preferably have the same meaning. Likewise compounds are preferred in which the radicals R have the same meaning.

The iminooxadiazine dione derivatives of the formula (I) can be prepared by reaction of diisocyanate trimers with iminooxadiazine dione structure, also called asymmetric trimers (AST) in the following, with hydroxy(meth)acrylates (X—OH, Y—OH or Z-OH) or mixtures of different hydroxy(meth)acrylates:

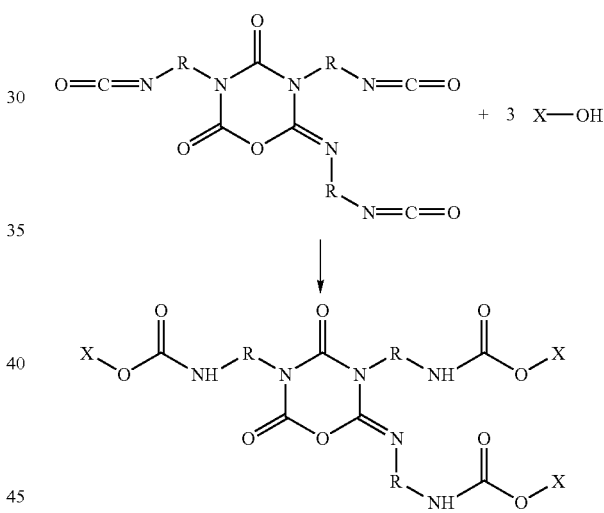

The asymmetric diisocyanate trimers are accessible analogously to the processes described in EP 0 798 299 A1 by trimerisation of commercially available diisocyanates, such as hexamethylene diisocyanate (HDI), 2,2,4- or 2,4,4-trimethylhexamethylene diisocyanate (TMDI), toluylene diisocyanate (TDI), m-xylylene diisocyanate (mXDI) or isophorone diisocyanate (IPDI). Mixtures of the asymmetric diisocyanate trimers with the corresponding symmetric trimers (ST) with isocyanurate structure and diisocyanate oligomers are obtained in this process. By higher oligomers are meant compounds which are formed from four and more diisocyanate monomers.

In the case of the (meth)acrylate-substituted iminooxadiazine dione derivatives according to the invention, in each case an isocyanate group of the diisocyanate is incorporated into the iminooxadiazine dione ring, while in each case the other isocyanate group together with the hydroxyl group of the hydroxy(meth)acrylates forms a urethane group via which the (meth)acrylate radicals are bound to the iminooxadiazine dione ring.

As the symmetric trimers and higher ogliomers occurring during the preparation of the iminooxadiazine dione derivatives likewise contain reactive isocyanate groups, they can also be converted in the described way to the corresponding (meth)acryl-substituted derivatives and need not therefore necessarily be separated from the iminooxadiazine dione derivatives. The total amount of the derivatives of symmetric trimers and higher oligomers should however be as small as possible and preferably amount to at most 50 wt.-%, particularly preferably at most 20 wt.-%, and quite particularly preferably at most 5 wt.-%, each relative to the total mass of diisocyanate trimers and diisocyanate oligomers. Ideally, the iminooxadiazine dione derivatives contain no symmetric trimers or higher oligomers.

The necessary OH-functionalized (meth)acrylates are either commercially available, such as e.g. HEMA, hydroxypropyl methacrylate (HPMA), 2-hydroxyethyl acrylate or GDMA, or can be prepared in the following ways (cf. e.g. C. Ferri, Reaktionen der organischen Synthese, G. Thieme Verlag, Stuttgart 1978): Baylis-Hillman reaction of acrylates with aldehydes which is catalysed by tertiary amines:

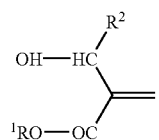

Concrete Example:

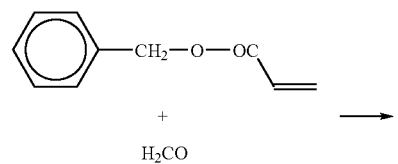

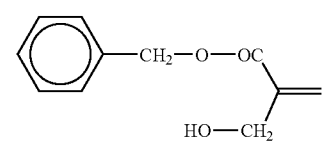

Unstoichometric esterification of dihydroxy compounds with (meth)acrylic acid or (meth)acrylic chloride:

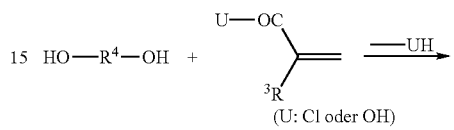

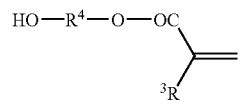

Concrete Example:

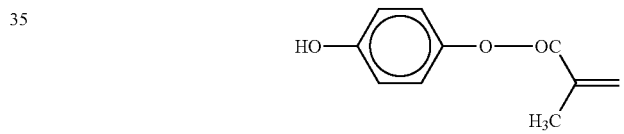

Particularly preferred examples of the (meth)acrylate-substituted, asymmetric diisocyanate trimers of formula (I) according to the invention are:

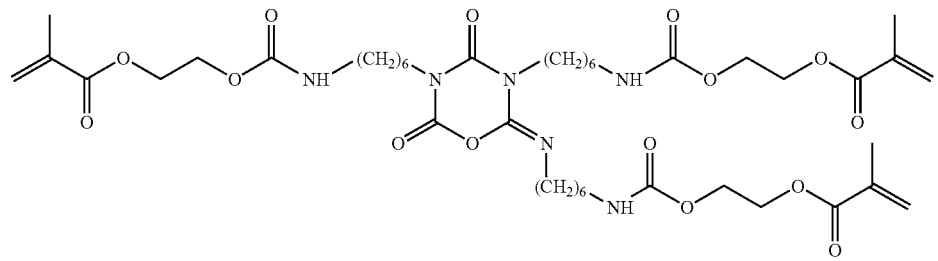

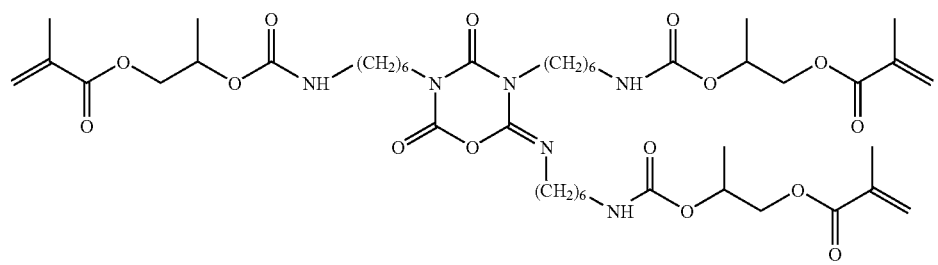

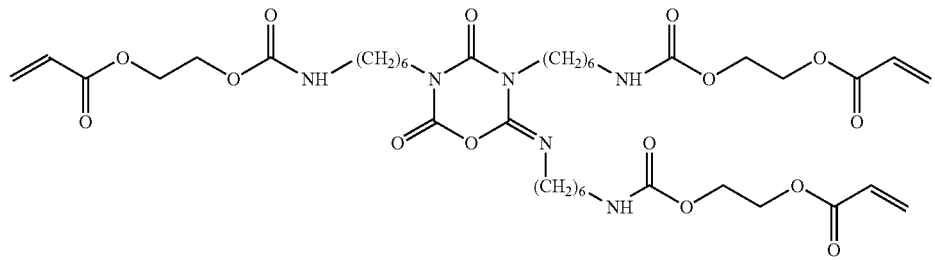
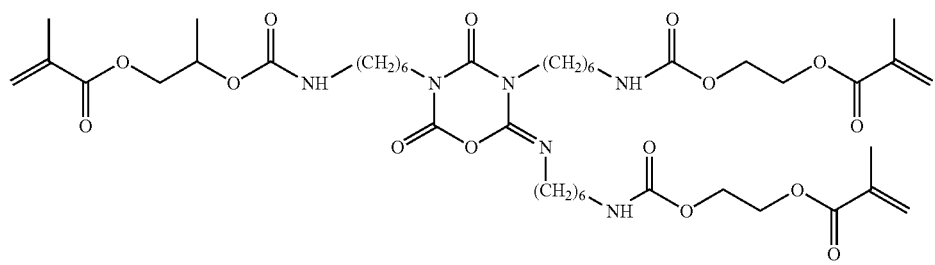
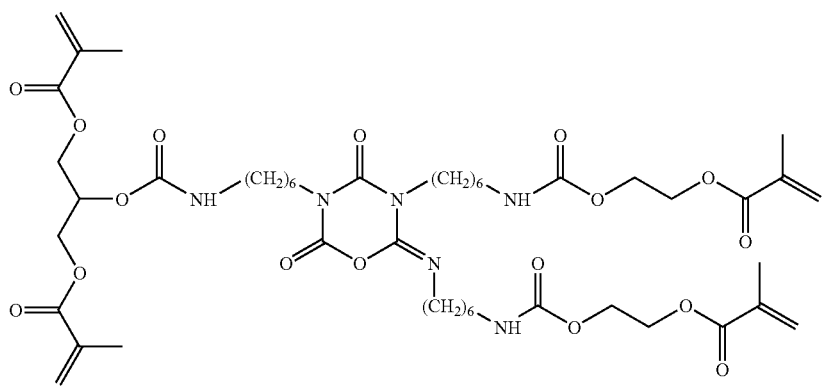
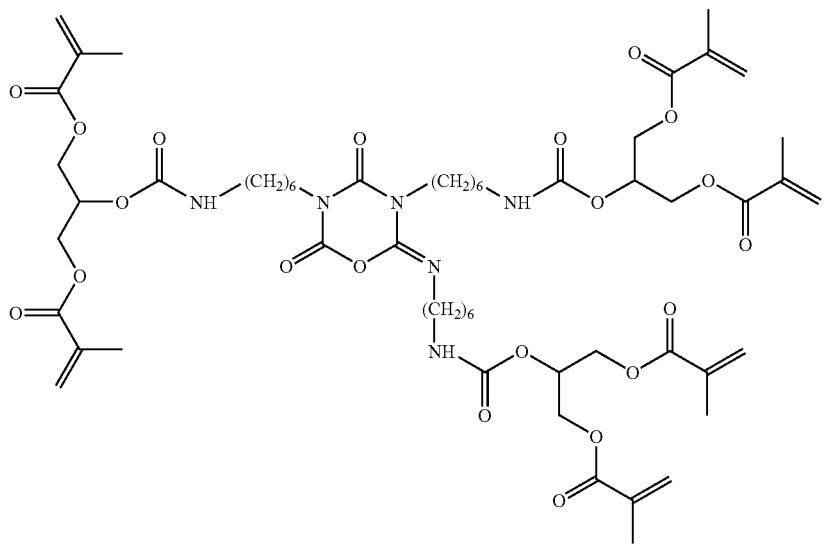

-continued

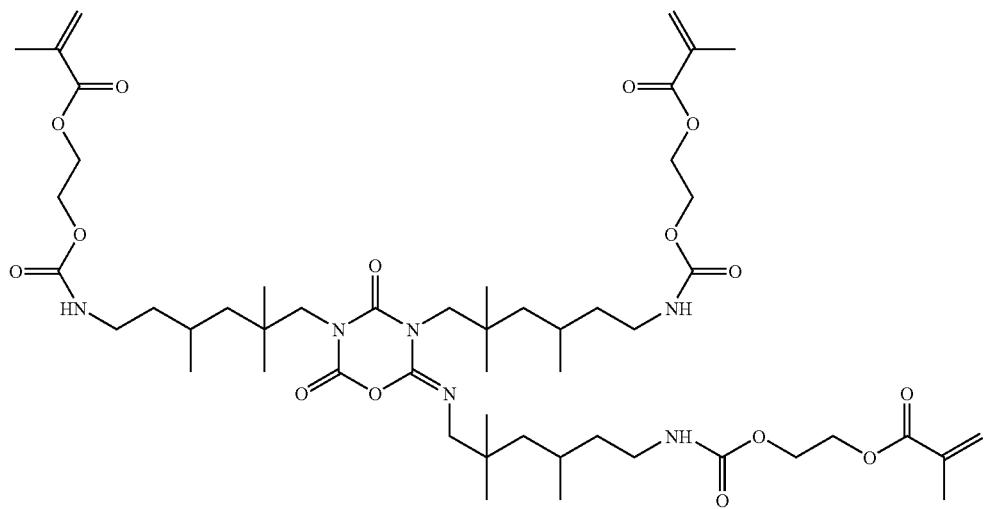

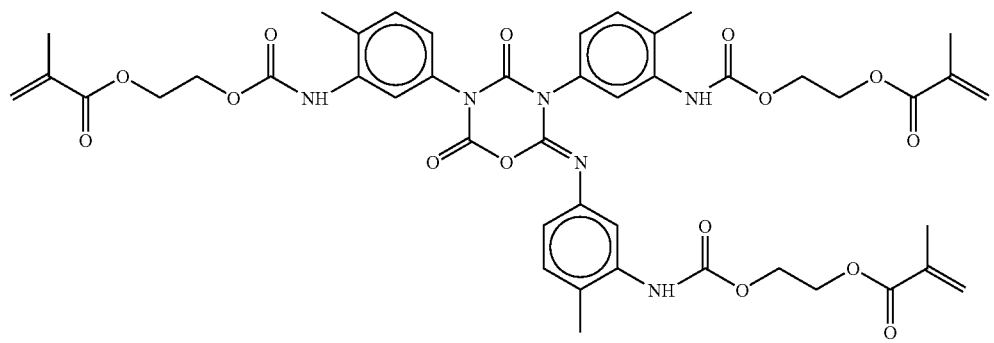

The iminooxadiazine dione derivatives according to the invention are suitable for the preparation of polymers, adhesives and in particular dental materials, such as filling composites, adhesives and cements, e.g. fixing cements. It is advantageous that a high cross-linking density can be achieved due to the functionality of the iminooxadiazine dione derivatives and that, due to the low viscosity, either materials with a high filler content or else materials with a low viscosity become accessible. Particularly readily-flowing and thus easily processable composites, so-called "flowable" filling composites, can therefore be prepared. Moreover the lower viscosity is advantageous above all in the case of adhesives.

Particularly suitable as dental materials are compositions which contain at least one iminooxadiazine dione derivative according to formula (I), preferably in combination with an initiator for the radical polymerization. According to a particularly preferred version the dental materials moreover additionally contain one or more radically polymerizable monomers and/or a particulate and/or fibrous filler.

The iminooxadiazine dione derivatives can be polymerized with the known radical initiators (cf. Encyclopaedia of Polymer Science and Engineering, Vol. 13, Wiley-Intersci. Pub., New York etc. 1988, 754ff). Azo compounds are preferred such as azobis(isobutyronitrile) (AIBN) or azobis-(4-cyanovaleric acid) or peroxides, such as dibenzoyl peroxide, dilauroyl peroxide, tert.-butylperoctoate, tert.-butylperbenzoate or di-(tert.-butyl)-peroxide. Benzopinacol and 2,2'-dialkylbenzopinacols are also suitable as initiators for the hot curing.

Photoinitiators are furthermore preferred (cf. J. P. Fouassier, J. F. Rabek (Eds.), Radiation Curing in Polymer Science and Technology, Vol. II, Elsevier Applied Science, London and New York 1993) for the UV or transparent range, such as benzoin ether, dialkylbenzilcetals, dialkoxyacetophenone, acylphosphinic oxides, α-diketones such as 9,10-phenanthrenequinone, diacetyl, anisil, 4,4'-dichlorobenzil and 4,4'-dialkoxybenzil and camphorquinone.

The iminooxadiazine dione derivatives can be polymerized alone or in a mixture with conventional radically polymerizable monomers, in particular with difunctional cross-linker monomers. Suitable for the preparation of adhesives or dental materials are above all cross-linking bi-, or polyfunctional acrylates or methacrylates, such as e.g. UDMA, which is accessible by reaction of 1 mol 2,2,4-trimethylhexamethylene diisocyanate with 2 mol 2-hydroxyethyl methacrylate (HEMA),

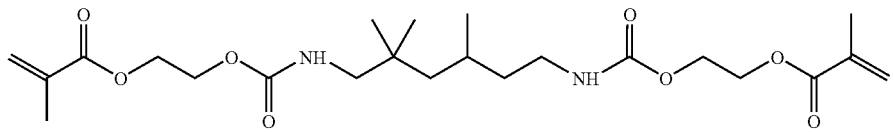

di- or triethylene glycol di(meth)acrylate (TEGDMA), decanediol di(meth)acrylate, trimethylolpropane tri(meth)acrylate, pentaerythritol tetra(meth)acrylate, as well as butanediol di(meth)acrylate, 1,10-decanediol di (meth)acrylate, 1,12-dodecanediol di(meth)acrylate, and in particular 2,2-bis-[4-(2'hydroxy-3'-methacryloxypropoxy)phenylene]propane (bis-GMA), which can be obtained by esterification of (meth)acrylic acid with the corresponding di- or polyols.

Particularly suitable as monofunctional monomers are methyl, ethyl, benzyl and furfuryl methacrylate as well as HEMA and hydroxypropyl methacrylate.

Moreover, the iminooxadiazine dione derivatives according to the invention or their mixtures can be filled with other radically polymerizable monomers with organic or inorganic particles or fibres to improve the mechanical properties. Preferred inorganic particulate fillers are amorphous spherical materials based on mixed oxides of $SiO_2$, $ZrO_2$ and/or $TiO_2$, microfine fillers, such as pyrogenic silica or precipitated silica, which preferably have an average primary particle size between 10 and 500 nm and a BET surface between 50 and 400 $m^2/g$, as well as macro- or minifillers, such as quartz, glass ceramics or glass powders as well as X-ray-opaque fillers, such as ytterbium trifluoride. Preferred fibrous fillers are glass fibres, synthetic fibres, in particular polyamide fibres, and carbon fibres. By macrofillers are meant fillers with an average particle size of 5 to 50 μm and a BET surface of preferably 1 to 10 $m^2/g$, by minifillers fillers with an average particle size of 0.5 to 5 μm and a BET surface of preferably 10 to 50 $m^2/g$.

Furthermore, if necessary, further components can be added, above all solvents, such as water, ethyl acetate or ethanol, as well as additives, such as stabilizers, UV absorbers, dyes or pigments, as well as lubricants.

Particularly preferred dental materials contain:

1 to 99 wt.-%, particularly preferably 5 to 80 wt.-%, quite particularly preferably 10 to 70 wt.-% and in particular 20 to 60 wt.-% iminooxadiazine dione derivative according to formula (I);

0.01 to 5 wt.-%, particularly preferably 0.1 to 2.0 wt.-% initiator for the radical polymerization;

0 to 80 wt.-%, particularly preferably 0 to 60 wt.-% and quite particularly preferably 0 to 50 wt.-% further radically polymerizable monomer;

0 to 90 wt.-% filler.

The exact composition of the dental materials depends on the desired application purpose. Dental materials for use as adhesives preferably contain:

1 to 80 wt.-%, particularly preferably 10 to 60 wt.-% iminooxadiazine dione derivative according to formula (I);

0.01 to 5 wt.-%, particularly preferably 0.1 to 2.0 wt.-% initiator for the radical polymerization;

0 to 60 wt.-%, particularly preferably 0 to 40 wt.-% further radically polymerizable monomer;

0 to 40 wt.-%, preferably 0 to 30 wt.-% solvent;

0 to 20 wt.-% filler.

Dental materials for use as cement preferably contain:

1 to 50 wt.-%, particularly preferably 20 to 44 wt.-% iminooxadiazine dione derivative according to formula (I);

0.01 to 5 wt.-%, particularly preferably 0.1 to 2.0 wt.-% initiator for the radical polymerization;

0 to 60 wt.-%, particularly preferably 0 to 24 wt.-% further radically polymerizable monomer;

20 to 60 wt.-%, particularly preferably 30 to 60 wt.-% filler.

Dental materials for use as filling composite preferably contain:

1 to 45 wt.-%, particularly preferably 10 to 33 wt.-% iminooxadiazine dione derivative according to formula (I);

0.01 to 5 wt.-%, particularly preferably 0.1 to 2.0 wt.-% initiator for the radical polymerization;

0 to 50 wt.-%, particularly preferably 5 to 25 wt.-% further radically polymerizable monomer;

30 to 85 wt.-%, particularly preferably 40 to 80 wt.-% filler.

The dental materials according to the invention are characterized vis-à-vis known materials of the same composition by a clearly lower viscosity and a better flowability so that the materials can be processed very much better. In addition, a higher cross-linking density and an improved incorporation of the iminooxadiazine dione derivative into the polymer network is achieved during polymerization, so that, after curing, the materials are superior to known materials in terms of their mechanical properties.

The preferred dental materials often have a greater or lesser filler content, which has to be homogeneously incorporated into the material in order to achieve the most uniform properties possible. The iminooxadiazine dione derivatives according to the invention have a clearly lower viscosity than for example the symmetric diisocyante trimers and thus quite considerably facilitate the homogeneous incorporation of fillers. In addition they permit the use of greater filler amounts, so that a better matching of the properties of the material to the desired application purpose is possible and further improvements to the mechanical properties of the cured materials are facilitated.

The invention is explained in more detail below with reference to embodiments.

EXAMPLES

Example 1

Reaction of the Asymmetric HDI Triisocyanate with HEMA 50.5 g (0.1 mol) of the asymmetric HDI triisocyanate (HDI-AST) (shear viscosity at 40° C.=1.3 Pas) were added dropwise at room temperature to a solution of 39 g (0.3 mol) HEMA, 12 mg TEMPO (2,2,6,6-tetramethyl-piperidine-1-oxyl, inhibitor), 25 mg MEHQ (hydroquinone monomethylether, stabilizer) and 0.2 g Metatin 812 (dibutyltin dioctoate, initiator) in 100 ml methylene chloride. After 20 hours stirring an isocyanate band was no longer to be recognized in the IR spectrum. The clear reaction mixture was washed twice each with 100 ml 1.0 N NaOH and three times each with 100 ml saturated brine. The organic phase was then dried with sodium sulfate, stabilized with 20 mg MEHQ and the solvent was completely removed at a rotary evaporator accompanied by the introduction of air. 60 g (yield: 67%) resulted of a product with a shear viscosity (40° C.) of 19.7 Pas which contains the trimethacrylate HDI-AST-HEMA of the following structure:

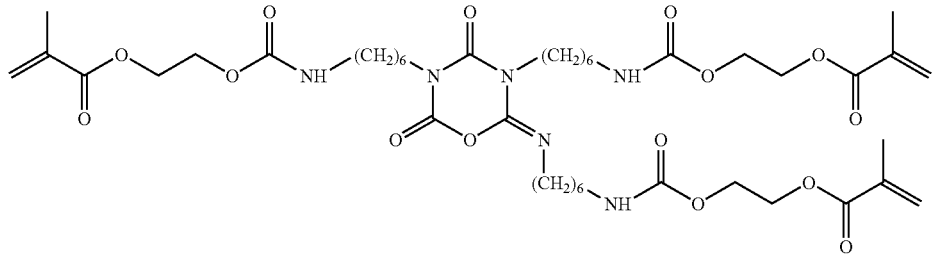

IR (ATR): 3368 (w), 2930 (m), 2858 (w), 1785 (w), 1682 (s), 1522 (m), 1458 (s) and 1163 (s) cm$^{-1}$.

$^1$H-NMR (CDCl$_3$): 1.35 (br, 12 H, CH$_2$), 1.51 (br, 6H, CH$_2$), 1.63 (br, 6H, CH$_2$), 1.94 (s, 9H, CH$_3$), 3.17 and 3.34 (t, sat. 6H, CH$_2$N), 3.84 (t, 6H, CH$_2$N), 4.31 (br, 12H, CH$_2$O), 5.02–5.03 (br, 3H, NH), 5.59 and 6.13 (2s, each 3H, =CH$_2$) ppm.

Example 2 (Comparison Example)

Reaction of the Symmetric HDI-triisocyanate with HEMA

Analogously to Example 1, 50.5 g (0.1 mol) of the symmetric HDI-triisocyanate (HDI-ST) Desmodur N 3300 from Bayer AG (shear viscosity at 40° C.=4.3 Pas) was reacted with 39 g (0.3 mol) HEMA and worked up. 69 g (yield: 77%) resulted of a product with a shear viscosity (40° C.) of 76.4 Pas which contains the trimethacrylate HDI-ST-HEMA of the following structure:

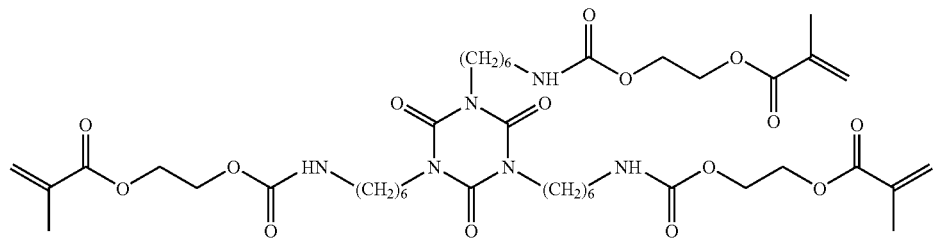

IR (ATR): 3367 (w), 2930 (m), 2858 (w), 1712 (w), 1677 (s), 1522 (m), 1459 (s) and 1164 (s) cm$^{-1}$.

$^1$H-NMR (CDCl$_3$): 1.35 (br, 12 H, CH$_2$), 1.50 (br, 6H, CH$_2$), 1.63 (br, 6H, CH$_2$), 1.95 (s, 9H, CH$_3$), 3.17 (t, 6H, CH$_2$N), 3.75 (t, 6H, CH$_2$N), 4.31 (br, 12H, CH$_2$O), 4.98 (br, 3H, NH), 5.59 and 6.33 (2s, each 3H, =CH$_2$) ppm.

Example 3

Reaction of the Asymmetric HDI-triisocyanate with HPMA

Analogously to Example 1, 50.5 g (0.1 mol) HDI-AST was reacted with 43.3 g (0.3 mol) HPMA and worked up. 56 g (yield: 59%) resulted of a product with a shear viscosity (40° C.) of 41.8 Pas which contains the trimethacrylate HDI-AST-HPMA of the following structure:

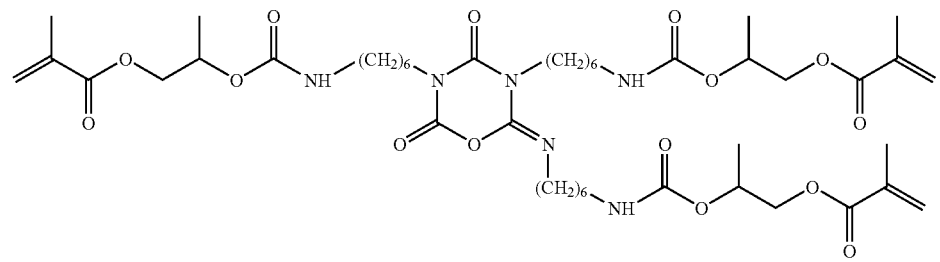

IR (ATR): 3366 (w), 2932 (m), 2858 (w), 1785 (w), 1678 (s), 1522 (m), 1459 (s) and 1156 (s) cm$^{-1}$.

$^1$H-NMR (CDCl$_3$): 1.24 (br, 9H, CH$_3$), 1.26 (br, 12H, CH$_2$), 1.51 (br, 6H, CH$_2$), 1.64 (br, 6H, CH$_2$), 1.94 (s, 9H, CH$_3$), 3.14 and 3.34 (t, sat. 6H, CH$_2$N), 3.84 (t, 6H, CH$_2$N), 4.14 (m, 6H, CH$_2$O), 4.93 (br, 3H, NH), 5.07–5.11 (m, 3H, CHO), 5.58 and 6.12 (2s, each 3H, =CH$_2$) ppm.

Example 4 (Comparison Example)

Reaction of the Symmetric HDI-triisocyanate with HPMA

Analogously to Example 1, 50.5 g (0.1 mol) HDI-ST Desmodur N 3300 was reacted with 43.3 g (0.3 mol) HPMA and worked up. 64 g (yield: 67%) resulted of a product with a shear viscosity (40° C.) of 77.0 Pas which contains the trimethacrylate HDI-ST-HPMA of the following structure:

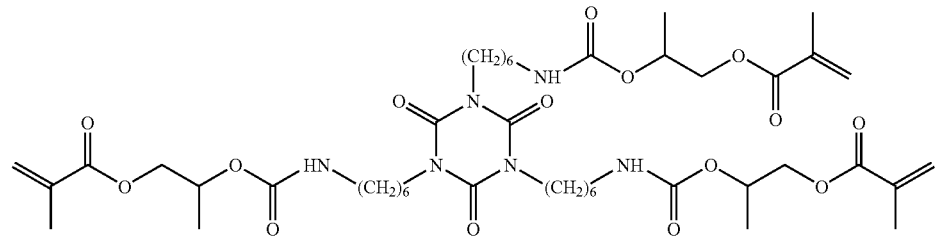

IR (ATR): 3366 (w), 2932 (m), 2858 (w), 1785 (w), 1678 (s), 1636 (w), 1522 (m), 1459 (s) and 1156 (s) cm$^{-1}$.

$^1$H-NMR (CDCl$_3$): 1.24 (br, 9H, CH$_3$), 1.27 (br, 12H, CH$_2$), 1.51 (br, 6H, CH$_2$), 1.64 (br, 6H, CH$_2$), 1.94 (s, 9H, CH$_3$), 3.14 (t, 6H, CH$_2$N), 3.86 (t, 6H, CH$_2$N), 4.09–4.20 (m, 6H, CH$_2$O), 4.93 (br, 3H, NH), 5.07–5.14 (br, m, 6H, CHO and NH), 5.56 and 6.11 (2s, each 3H, =CH$_2$) ppm.

Example 5

Reaction of the Asymmetric HDI-triisocyanate with GDMA

Analogously to Example 1, 50.5 g (0.1 mol) HDI-AST was reacted with 68.2 g (0.3 mol) GDMA and worked up. 52 g (yield: 44%) resulted of a product with a shear viscosity (40° C.) of 92.8 Pas which contains the hexamethacrylate HDI-AST-GDMA of the following structure:

IR (ATR): 3370 (w), 2930 (m), 2858 (w), 1713 (s), 1683 (s), 1523 (m), 1460 (s) and 1149 (s) cm$^{-1}$.

$^1$H-NMR (CDCl$_3$): 1.35 (br, 12H, CH$_2$), 1.50 (br, 6H, CH$_2$), 1.63 (br, 6H, CH$_2$), 1.94 (s, 9H, CH$_3$), 3.17 and 3.34 (t, sat. 6H, CH$_2$N), 3.85(t, 6H, CH$_2$N), 3.25–4.40 (m, 12H, CH$_2$O), 4.91 (br, 3H, NH), 5.27–5.31 (br, 3H, CHO), 5.60 and 6.11 (2s, each 6H, =CH$_2$) ppm.

Example 6 (Comparison Example)

Reaction of the Symmetric HDI Triisocyanate with GDMA

Analogously to Example 1, 50.5 g (0.1 mol) HDI-ST Desmodur N 3300 was reacted with 68.2 g (0.3 mol) GDMA and worked up. 80 g (yield: 68%) resulted of a product with a shear viscosity (40° C.) of 149.0 Pas which contains the hexamethacrylate HDI-ST-GDMA of the following structure:

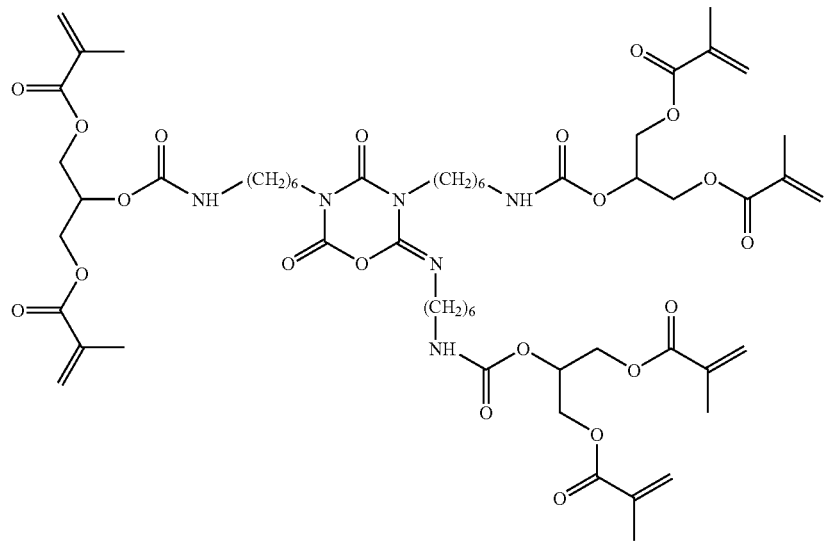

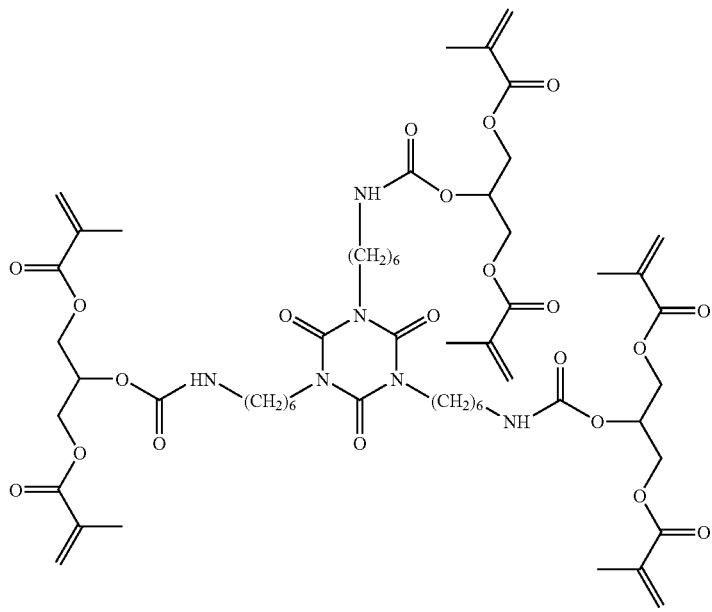

A comparison of examples 1 and 2, 3 and 4 as well as 5 and 6 shows that the methacrylate-substituted asymmetric diisocyanate trimers according to the invention have a clearly lower viscosity compared with the corresponding symmetric diisocyanate trimers.

Example 7

Preparation of Composite Pastes Based on the Methacrylate-substituted Diisocyanate Trimers of Examples 1 to 4

For the preparation of composite pastes the components named in the following table were mixed together in the stated amounts using a triple-roller mill of the Exact type (Exact Apparatebau) and then the complex viscosity of the compositions was measured.

Composition of the examined composite pastes

| Component | Paste 1 | Paste 2 | Paste 3 | Paste 4 |
|---|---|---|---|---|
| Trimer from Ex. 1 | 20 | — | — | — |
| Trimer from Ex. 2*) | — | 20 | — | — |
| Trimer from Ex. 3 | — | — | 20 | — |
| Trimer from Ex. 4*) | — | — | — | 20 |
| Bis-GMA | 20 | 20 | 20 | 20 |
| silanized glass filler[1)] | 37.8 | 37.8 | 37.8 | 37.8 |
| Sphärosil[2)] | 10.5 | 10.5 | 10.5 | 10.5 |
| pyrogenic silica[3)] | 0.7 | 0.7 | 0.7 | 0.7 |
| YbF$_3$[4)] | 11.0 | 11.0 | 11.0 | 11.0 |
| Complex viscosity[5)] | 2.21 | 3.36 | 2.20 | 2.79 |

*)Comparison example
[1)]Barium-aluminium-boron silicate glass powder (55 wt.-% $SiO_2$, 25 wt.-% BaO, 10 wt.-% $B_2O_3$, 10 wt.-% $Al_2O_3$, silanized with 3-methacryloyloxypropyltrimethoxy silane, average particle size approx. 1 μm (Schott)
[2)]$SiO_2$—$ZrO_2$ mixed oxide (approx. 25 wt.-% $ZrO_2$) with a primary particle size of 130–230 nm (Tokoyama Soda)
[3)]OX-50, primary particle size 40 nm (Degussa)
[4)]Ytterbium fluoride (Rhone-Poulenc)
[5)]Determined with aCVO 120 type rheometer (Bohlin Instruments) at 23° C. with a shear rate of 1 Hz The results summarized in the table prove that the methacrylate-substituted asymmetric diisocyanate trimers according to the invention result in composite pastes with a clearly reduced viscosity, compared with the corresponding symmetric trimers with the same filler content, which have a significantly better flow behaviour and processability. The materials are characterized by a good matching to the hard tooth substance.

Alternatively, compositions can be prepared which, with the same viscosity, have a higher filler content and thus better mechanical properties and a lower polymerization shrinkage.

The invention claimed is:

1. Dental cement comprising:
   1 to 50 weight % iminooxadiazine dione derivative with the formula (I)

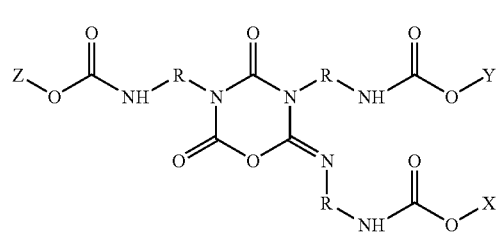

in which
X, Y and Z represent a (meth)acrylic acid radical of the formula (II)

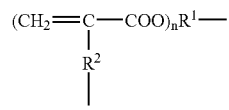

in which

R¹ is hydrogen, an aliphatic hydrocarbon radical with 1 to 14 carbon atoms, which can be interrupted by oxygen atoms, or an aromatic hydrocarbon radical with 6 to 16 carbon atoms, R² is hydrogen, an aliphatic hydrocarbon radical with 1 to 5 carbon atoms or an aromatic hydrocarbon radical with 6 carbon atoms, only one of the radicals R¹ and R² being able to have the meaning hydrogen;

n is 1 or 2;

where the (meth)acrylic acid radical of formula (II) is bound to the radical of formula (I) via R¹ or R² and the binding point remaining at R² or R¹ is saturated by hydrogen, and where X, Y and Z can be the same or different; the individual radicals R can be the same or different and selected from alicyclic or aromatic hydrocarbon radicals with 5 to 10 carbon atoms or aliphatic hydrocarbon radicals with 1 to 10 carbon atoms;

0.01 to 5 weight % initiator for the radical polymerization;

0 to 60 weight % further radically polymerizable monomer; and 20 to 60 weight % filler.

2. The dental cement according to claim 1, wherein the (meth)acrylic acid radical of formula (II) has a structure of formula (IIa), (IIb) or (IIc), $$CH_2=C(R^{2a})-COOR^{1a}\quad\text{Formula IIa}$$
with CH— branch $$CH_2=C(R^{2b})-COOR^{1b}-\quad\text{Formula IIb}$$

$$\begin{array}{l}CH_2=C(R^{2c})-COO-CH_2\\ \quad\quad\quad\quad\quad\quad\quad\quad\quad CH-\\ CH_2=C(R^{2c})-COO-CH_2\end{array}\quad\text{Formula IIc}$$

where $R^{1a}$ is hydrogen or a straight-chained $C_1$ to $C_{12}$ alkyl radical, a $C_6$ to $C_{12}$ aryl radical or $C_7$ to $C_{16}$ alkylaryl radical, $R^{2a}$, is hydrogen, a $C_1$ to $C_5$ alkyl radical or a phenyl radical;

$R^{1b}$ is a $C_1$ to $C_{14}$ alkylene radical which can be interrupted by oxygen atoms, or a phenylene radical;

$R^{2b}$ is hydrogen or a methyl radical;

$R^{2c}$ is hydrogen or a methyl radical.

3. The dental cement according to claim 1, wherein the radicals R are selected from the group which consists of the hexamethylene, 2,2,4-trimethylhexamethylene, 2,4,4-trimethylhexamethylene, m-toluylene, m-xylylene and isophorone radical.

4. The dental cement according to claim 2, wherein at least one of the following radicals has one of the following meanings R=hexamethylene, 2,2,4-trimethylhexamethylene, 2,4,4-trimethylhexamethylene or m-toluylene;

$R^{1a}$=methyl, ethyl, benzyl or phenyl;

$R^{2a}$=hydrogen or methyl;

$R^{1b}$=ethylene, methylethylene or propylene;

$R^{2b}$=hydrogen or methyl;

$R^{2c}$=hydrogen or methyl.

5. The dental cement according to claim 1, wherein X, Y and Z have the same meaning.

6. The dental cement according to claim 1, comprising 20 to 44 weight % of the iminooxadiazine dione derivative.

7. The dental cement according to claim 1, comprising 0.1 to 2.0 weight % initiator for the radical polymerization.

8. The dental cement according to claim 1, comprising 30 to 60 wt.-% filler.

9. Dental filling composite comprising:

1 to 45 weight % iminooxadiazine dione derivative with the formula (I)

$$Z-O-C(=O)-NH-R-N\underset{\underset{N-R-NH-C(=O)-O-X}{|}}{\overset{\overset{C(=O)}{|}}{\underset{\underset{}{}}{}}}-N-R-NH-C(=O)-O-Y$$
(iminooxadiazine dione core with three urethane arms bearing X, Y, Z)

in which

X, Y and Z represent a (meth)acrylic acid radical of the formula (II)

$$(CH_2=C(R^2)-COO)_n R^1-$$

in which

R¹ is hydrogen, an aliphatic hydrocarbon radical with 1 to 14 carbon atoms, which can be interrupted by oxygen atoms, or an aromatic hydrocarbon radical with 6 to 16 carbon atoms, R² is hydrogen, an aliphatic hydrocarbon radical with 1 to 5 carbon atoms or an aromatic hydrocarbon radical with 6 carbon atoms, only one of the radicals R¹ and R² being able to have the meaning hydrogen;

n is 1 or 2;

where the (meth)acrylic acid radical of formula (II) is bound to the radical of formula (I) via R¹ or R² and the binding point remaining at R² or R¹ is saturated by hydrogen, and where X, Y and Z can be the same or different; the individual radicals R can be the same or different and selected from alicyclic or aromatic hydrocarbon radicals with 5 to 10 carbon atoms or aliphatic hydrocarbon radicals with 1 to 10 carbon atoms;

0.01 to 5 weight % initiator for the radical polymerization;

0 to 50 weight % further radically polymerizable monomer; and 30 to 85 weight % filler.

10. The dental filling composite according to claim 9, comprising 10 to 33 weight % of the iminooxadiazine dione derivative.

11. The dental filling composite according to claim 9, comprising 0.1 to 2.0 weight % initiator for the radical polymerization.

12. The dental filling composite according to claim 9, comprising 40 to 80 wt.-% filler.

* * * * *